(12) United States Patent
Rodniansky et al.

(10) Patent No.: US 11,632,380 B2
(45) Date of Patent: Apr. 18, 2023

(54) IDENTIFYING LARGE DATABASE TRANSACTIONS

(71) Applicant: International Business Machines Corporation, Armonk, NY (US)

(72) Inventors: Leonid Rodniansky, Allston, MA (US); Peter Maniatis, Clinton, MA (US); Tania Butovsky, Needham, MA (US); Dmitri Dodor, Pepperell, MA (US)

(73) Assignee: International Business Machines Corporation, Armonk, NY (US)

( * ) Notice: Subject to any disclaimer, the term of this patent is extended or adjusted under 35 U.S.C. 154(b) by 364 days.

(21) Appl. No.: 16/821,083

(22) Filed: Mar. 17, 2020

(65) Prior Publication Data

US 2021/0297426 A1   Sep. 23, 2021

(51) Int. Cl.
*H04L 9/40* (2022.01)
*G16H 10/00* (2018.01)
*G06F 16/22* (2019.01)
*H04L 9/32* (2006.01)
*G06Q 50/26* (2012.01)

(52) U.S. Cl.
CPC ...... *H04L 63/1416* (2013.01); *G06F 16/2246* (2019.01); *G06Q 50/265* (2013.01); *G16H 10/00* (2018.01); *H04L 9/3234* (2013.01); *H04L 9/3236* (2013.01)

(58) Field of Classification Search
CPC ........... H04L 63/1416; H04L 63/1425; H04L 63/1466; H04L 9/3234; H04L 9/3236; G06F 16/2246; G06Q 50/265; G16H 10/00
See application file for complete search history.

(56) References Cited

U.S. PATENT DOCUMENTS

| 8,930,380 | B1 | 1/2015 | Saurabh et al. |
| 9,552,412 | B1* | 1/2017 | Lowe ................. G06F 16/3325 |
| 9,888,034 | B2 | 2/2018 | Liu et al. |
| 2003/0106049 | A1 | 6/2003 | Ungar |
| 2008/0072134 | A1 | 3/2008 | Balakrishnan et al. |
| 2014/0244680 | A1 | 8/2014 | Chandran et al. |
| 2015/0227624 | A1* | 8/2015 | Busch ............... G06F 16/24578 707/728 |

(Continued)

OTHER PUBLICATIONS

Oracle, "A.3 Logical Database Limits", Database Reference, printed Nov. 21, 2019, 2 pages <https://docs.oracle.com/en/database/oracle/oracle-database/12.2/refrn/logical-database-limits.html#GUID-685230CF-63F5-4C5A-B8B0-037C566BDA76>.

(Continued)

*Primary Examiner* — Han Yang
(74) *Attorney, Agent, or Firm* — Donald J. O'Brien (57) ABSTRACT

Embodiments are disclosed for a method for identifying large database transactions. The method includes generating a token marker sequence of a database transaction. The token marker sequence includes multiple token markers. The token markers include a token of the database transaction and a position corresponding to the token. The method further includes sorting the token markers based on a probability that the token occurs in a stream of database transactions. Additionally, the method includes reducing a size of the token marker sequence based on a predetermined threshold.

17 Claims, 9 Drawing Sheets

(56) References Cited

U.S. PATENT DOCUMENTS

| | | | | |
|---|---|---|---|---|
| 2016/0179981 | A1* | 6/2016 | Enoki | G06F 16/319 707/800 |
| 2018/0121326 | A1* | 5/2018 | Qi | G06F 11/3636 |
| 2019/0207974 | A1* | 7/2019 | Jas | G06F 21/6227 |
| 2021/0224281 | A1* | 7/2021 | Lee | G06F 16/24561 |
| 2021/0326347 | A1* | 10/2021 | Yoshida | G06F 16/316 |

OTHER PUBLICATIONS

Wikipedia, "Abstract syntax tree", From Wikipedia, the free encyclopedia, last edited on Sep. 9, 2019, 5 pages <https://en.wikipedia.org/wiki/Abstract_syntax_tree>.

Miller, B., "Scalable Platform for Malicious Content Detection Integrating Machine Learning and Manual Review", A dissertation submitted in partial satisfaction of the requirements for the degree of Doctor of Philosophy in Computer Science, Summer 2015, 113 pages.

Newsome et al., "Polygraph: Automatically generating signatures for polymorphic worms", Proceedings of the 2005 IEEE Symposium on Security and Privacy, 16 pages.

Kim et al., "Autograph: Toward Automated, Distributed Worm Signature Detection", Security '04 Paper, Nov. 11, 2019, 29 pages.

Drew et al., "Polymorphic malware detection using sequence classification methods and ensembles", BioSTAR 2016 Recommended Submission—EURASIP Journal on Information Security, 2017, 12 pages.

Kong et al., "SAS: semantics aware signature generation for polymorphic worm detection", Int. J. Inf. Secur. (2011), Published online: May 22, 2011, pp. 269-283.

Rajesh, S., "Protection from application layer DDoS attacks for popular websites", International Journal of Computer and Electrical Engineering, vol. 5, No. 6, Dec. 2013, 4 pages.

Amirtahmasebi et al., "A survey of SQL injection defense mechanisms", Chapter 10, Copyright 2012, 3 pages.

Mell et al., "The NIST Definition of Cloud Computing", Recommendations of the National Institute of Standards and Technology, Sep. 2011, 7 pages.

\* cited by examiner

IDENTIFYING LARGE DATABASE TRANSACTIONS

BACKGROUND

The present disclosure relates to databases, and more specifically, to identifying large database transactions.

Databases are computer software and/or hardware architectures that store data and provide access to the stored data. Accessing the stored data can mean retrieving and analyzing data to produce reporting and the like. Additionally, accessing the stored data can mean making updates to the stored data. However, in some cases, a malicious actor, such as a hacker, can exploit this access to corrupt the database (or its users). Accordingly, a database protection solution (DPS) can monitor database access to identify potential attacks.

SUMMARY

Embodiments are disclosed for a method for identifying large database transactions. The method includes generating a token marker sequence of a database transaction. The token marker sequence includes multiple token markers. The token markers include a token of the database transaction and a position corresponding to the token. The method further includes sorting the token markers based on a probability that the token occurs in a stream of database transactions. Additionally, the method includes reducing a size of the token marker sequence based on a predetermined threshold.

Further aspects of the present disclosure are directed toward systems and computer program products with functionality similar to the functionality discussed above regarding the computer-implemented methods. The present summary is not intended to illustrate each aspect of every implementation of, and/or every embodiment of the present disclosure.

BRIEF DESCRIPTION OF THE DRAWINGS

The drawings included in the present application are incorporated into and form part of the specification. They illustrate embodiments of the present disclosure and, along with the description, serve to explain the principles of the disclosure. The drawings are only illustrative of certain embodiments and do not limit the disclosure.

While the present disclosure is amenable to various modifications and alternative forms, specifics thereof have been shown by way of example, in the drawings and will be described in detail. It should be understood, however, that the intention is not to limit the present disclosure to the particular embodiments described. On the contrary, the intention is to cover all modifications, equivalents, and alternatives falling within the spirit and scope of the present disclosure.

DETAILED DESCRIPTION

A database can store data in tables containing rows of columns. A column can represent a single attribute of a record, such as the last name of a medical patient. The row can include multiple columns describing different attributes of the patient, for example. A table can represent a larger level of organization, including multiple rows, such as for multiple medical patients.

In some cases, accessing the stored data can involve executing transactions against the database. A transaction can identify tables, rows, and columns for retrieval and/or updating. The database can receive the transactions in a stream and use a DPS to check each transaction for potential security threats before executing the transaction against the database.

In order to detect potential security threats, the DPS can parse the transactions based on the database language syntax of the transaction. Parsing can involve identifying individual tokens, e.g., words, in the transaction, identifying the context of the token with respect to the syntax, and generating complex mathematical models to represent the transactions. Generating these models makes it possible to identify patterns of potential attacks. The models may be based on the tables, rows, and columns identified in the transaction. While databases may put some limits on the number of columns in a row, a database may allow an unlimited number of rows and tables. As such, the potential sizes involved can incur a challenging level of computational complexity. Due to this computational complexity, in some cases, parsing can slow the performance of the database. Additionally, this slowed performance can prevent the DPS from protecting the database in real-time.

Further, a DPS could become overwhelmed by a Denial-of-Service (DoS)-like attack if the DPS is flooded with transactions incurring a relatively high computational complexity for the DPS's parser. A DoS attack denies a web server, for example, the ability to respond to any requests from networked computers. The DoS attack accomplishes this by flooding the web server (in this example) with so many requests that the physical resources of the web server become overwhelmed and potentially crash the web server. A similar type of attack is possible on databases using relatively large numbers of relatively highly complex transactions. Thus, a DPS can be effectively crippled by a DoS attack as a by-product of relatively long and complex transactions being executed on the database.

Accordingly, some embodiments of the present disclosure can represent these large and complex transactions as a limited set of tokens sequenced in such a way that the transactions can be deemed unique or repeated. Thus, when the DPS receives multiple copies of relatively large transactions, the DPS parsing phase can be skipped, thus avoiding the overhead associated with repeated parsing. In this way, some embodiments can thus avoid the potential for a DoS on the DPS that may be attempted using relatively large and complex transactions.

Figure 1:
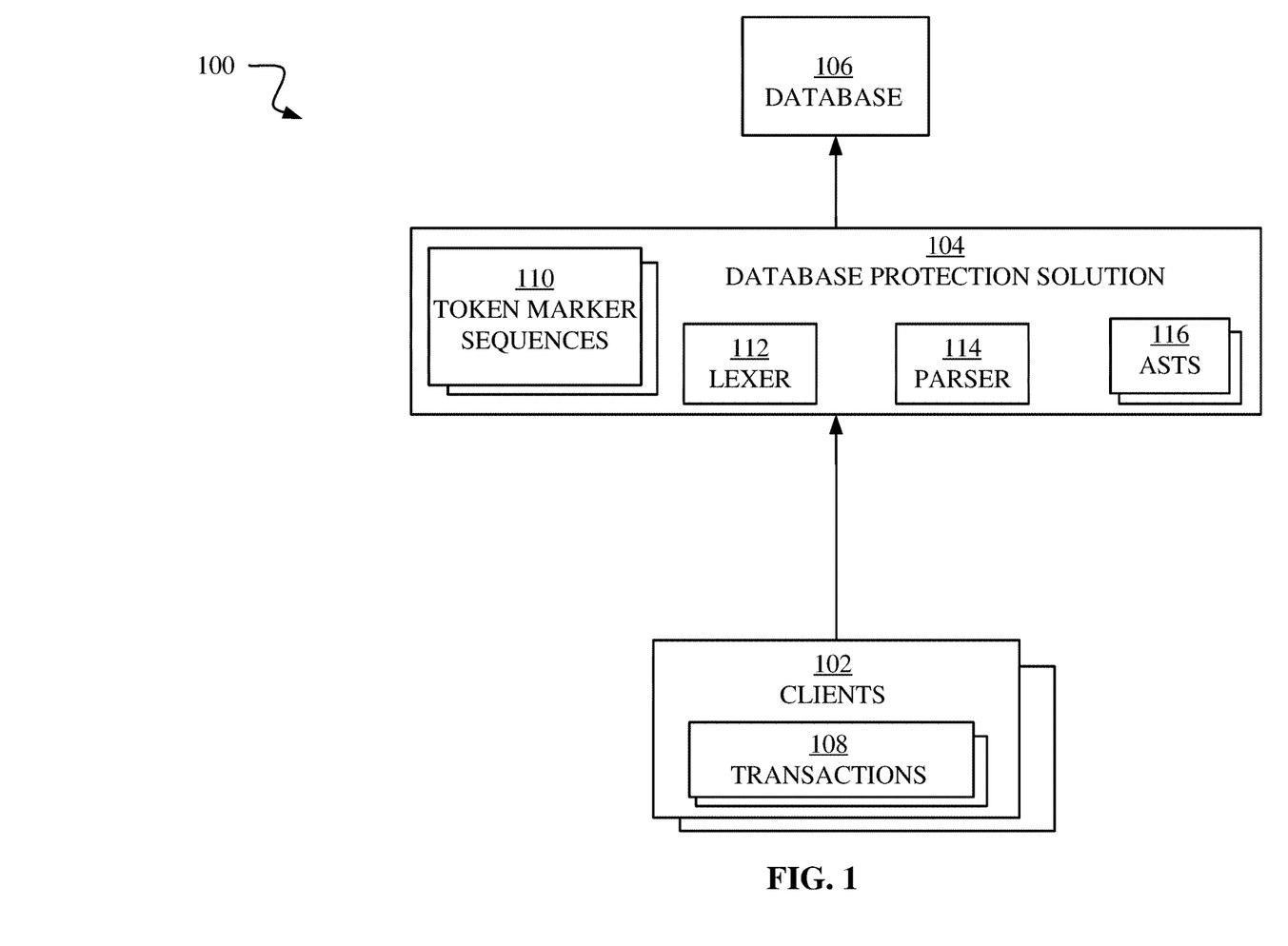
FIG. 1 is a block diagram of an example system for identifying large database transactions, in accordance with some embodiments of the present disclosure.

FIG. 1 is a block diagram of an example system 100 for identifying large database transactions, in accordance with some embodiments of the present disclosure. The system 100 includes clients 102, database protection system 104, and database 106.

The clients 102 can be computer systems that make requests to the database 106 to execute transactions 108. The clients 102 can generate the transactions 108 in order to retrieve and/or update data in tables of the database 106. Below, the EXAMPLE structured query language (SQL) 1 can represent a transaction 108:
SELECT movieTitle FROM StarsIn, MovieStar WHERE starName-'Adriano' AND birthDate LIKE '%1999'

Example SQL 1

The syntax of SQL describes each command, such as EXAMPLE SQL 1, as a set of tokens. The tokens can include commands, command syntax, table names, column names, and variables. The commands and command syntax can be capitalized. In EXAMPLE SQL 1, the token, SELECT, is a command, and the tokens, FROM, WHERE, AND, and LIKE are command syntax.

Table and column names can be mixed case, where table names capitalize the first letter of each word. Column names can use lower case for the first word and capitalize the first letter in subsequent words. Accordingly, the EXAMPLE SQL 1 is a command to select the column, movieTitle, from the tables, StarsIn and MovieStar. Additionally, the command syntax further specifies conditions for selecting specific rows from the tables. More specifically, the rows selected are those with the value for column starName=to the variable, 'Adriano.' Additionally, the rows selected are those with the value for column birthdate LIKE '%1999.' The command syntax LIKE specified in this example can indicate that a birthdate with a value containing the variable, '1999,' is a match.

The DPS 104 can monitor the transactions 108 to identify suspicious behavior in real-time. Identifying suspicious behavior in real-time can mean identifying a potentially malicious transaction before executing the transaction against the database 106. Accordingly, the DPS 104 can generate an alert when the DPS 104 detects a security violation or anomalies.

If the DPS 104 does not identify suspicious behavior, the database 106 can execute the transaction 108 and generate a result. The result can be a report generated by the transaction 108. For example, the result from EXAMPLE SQL 1 can include a list of movie titles starring actors named Adriano and born in 1999. Further, the database 106 can use a network to provide the result to the client 102 that sent the corresponding transaction 108.

The DPS 104 can include a lexer 112, parser 114, abstract syntax trees (ASTS) 116, and token marker sequences 110. The parser 114 can generate an AST 116 based on the transaction·108. Further, the DPS 104 can analyze the AST 116 to determine if the transaction 108 is a threat.

Abstract syntax trees are useful for representing statements with syntactic structure. Statements with syntactic structure can range from human languages to the source code of an SQL or other computer programming language. Further, abstract syntax trees can be graphical representations of nodes in a tree-like structure with a root, branches, and leaves. Each node of the abstract syntax tree can represent a token of source code. Additionally, abstract syntax trees can be abstract in the sense that abstract syntax trees may not include all the tokens of a particular statement.

Thus, the ASTS 116 represent the transactions 108. However, generating ASTS 116 for relatively large, complex transactions can be costly in terms of computer time. Accordingly, in some embodiments of the present disclosure, the lexer 112 can generate a unique identifier that corresponds to the AST 116 that the parser 114 generates for the transaction 108. Further, the lexer 112 can store the unique identifier in the token marker sequences 110.

The token marker sequences 110 can be a subset of token markers that identify the token and the column position of the first character of the token in the transaction 108. In some embodiments of the present disclosure, the token marker sequences 110 can include the relatively least frequently encountered tokens of each of the transactions 108. The number of tokens in the token marker sequences 110 can be determined based on a predetermined threshold. For example, a threshold probability can limit the tokens in the token marker sequence 110 to the tokens below the token threshold. The number of tokens can be a minimized set that only needs to identify the subset of tokens that uniquely identify the transaction 108.

In some embodiments, the token marker sequences 110 can be sorted in ascending order of the probability that the token marker appears in the stream of transactions 108. In this way, the token marker sequences 110 can uniquely identify the transactions 108. Further, representing the transactions 108 in this way makes it possible for the parser 114 to determine if the DPS 104 is receiving duplicate transactions as part of a potential DoS-style attack. Thus, if the DPS 104 receives a duplicate transaction as indicated by the token marker sequence 110, the DPS 104 can spare the parser 114 the overhead of re-parsing a previously parsed transaction 108.

A token marker includes a token name and the beginning position number in the transaction 108 where the token appears. The probability can be based on a rolling total of the number of times that each token appears in the stream of transactions 108. Alternatively, other approaches for determining probability may be used such as a sliding window probability over some period of time, fixed or not, or by using a probabilistic learning phase. In some embodiments of the present disclosure, the lexer 112 can group the token marker sequences 110 using a common hash of a predetermined number of characters starting at the beginning of the transaction 108. In this way, the DPS 104 can group token marker sequences 110 for similar transactions.

Thus, as the DPS 104 processes additional transactions 108, the DPS 104 can use the token marker sequences 110 to determine if the parser 114 has already generated an AST 116 that can be used for the security analysis of the DPS 104. In this way, the DPS 104 can save time by not re-generating an AST 116 for every transaction.

One possible approach to generate unique identifiers for transactions is to use a hashing algorithm that can uniquely encode transactions. However, hashing relatively large, complex transactions can use relatively large amounts of computer time. Further, hashing such transactions can distinguish transactions 108 that could use the same AST 116. For example, EXAMPLE SQL 2 and EXAMPLE SQL 3 represent similar SQL statements that can use the same AST 116.

SELECT movieTitle FROM StarsIn, MovieStar WHERE starName='Adriano' AND birthDate LIKE '%1999'

Example SQL 2

SELECT movieTitle FROM StarsIn, MovieStar WHERE starName='Chelentano' AND birthDate LIKE '%1999'

Example SQL 3

Because the EXAMPLE SQLS 2 and 3 are similar, the parser 114 may generate the same ASTS 116 for the EXAMPLE SQLS 2 and 3. However, the hashes for EXAMPLE SQLS 2 and 3 can be different because of the difference in the literal values: Adriano and Chelentano.

Figure 2:
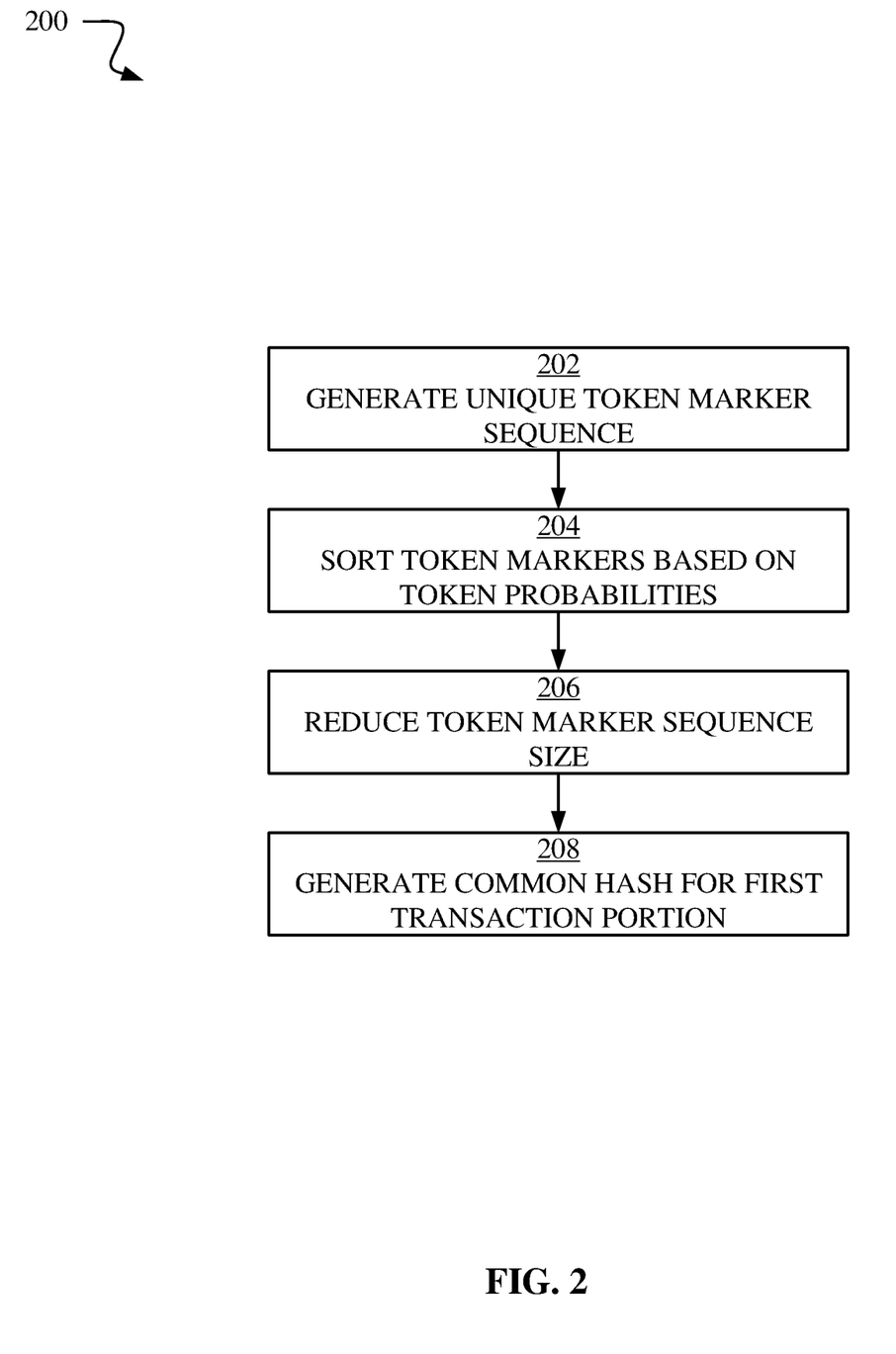
FIG. 2 is a process flow diagram of a method for generating a token marker sequence for a transaction, in accordance with some embodiments of the present disclosure.

FIG. 2 is a process flow diagram of a method 200 for generating a token marker sequence 110 for a transaction 108, in accordance with some embodiments of the present disclosure. The method 200 can be performed by a lexer, such as the lexer 112 described with respect to FIG. 1.

Referring back to FIG. 2, at operation 202, the lexer 112 can generate a unique token marker sequence 110 such as the token marker sequence 110. The unique token marker sequence 110 can include a limited set of token sequences with their corresponding positions in the transactions 108. In embodiments of the present disclosure, common syntax tokens, such as reserved words, operators, and symbols, can be excluded from the token marker sequences 110. In some embodiments, the unique token marker sequence 110 can include the table and column names from the transaction 108.

For example, a token marker sequence 110 for the EXAMPLE SQL 3 can include the token markers: movieTitle:8, StarsIn:24, MovieStar:33, starName:49, and birthday:73, wherein the numerals represent the position of the respective tokens in the EXAMPLE SQL 3. Accordingly, the lexer 112 can generate the EXAMPLE TOKEN MARKER SEQUENCE 1 for EXAMPLE SQL 3:
{movieTitle:8, StarsIn:24, MovieStart:33, starName:49, birthDate:73}
Example Token Marker Sequence 1

At operation 204, the lexer 112 can sort the token markers in ascending order of the token probabilities. The token probabilities can represent the probability that each token appears in the stream of transactions 108. Thus, if the token probabilities for the movieTitle, StarsIn, MovieStar, starName, and birthDate tokens are, respectively: 10%, 7%, 8%, 3%, and 4%, the lexer 112 can sort the token markers as shown in EXAMPLE TOKEN MARKER SEQUENCE 2:
{starName:49, birthDate:73, StarsIn:24, MovieStar:33, movieTitle:8}
Example Token Marker Sequence 2

At operation 206, the lexer 112 can reduce the token marker sequence size. In a lexed statement, each token marker would represent exactly 1 non-overlapping portion of the input. In some embodiments, reducing the token marker sequence size includes minimizing the token marker sequence size, where minimization would thus include reducing the number of token markers in a given sequence to the minimum number that is required to identify the statement uniquely. At operation 208, the lexer 112 can generate a common hash for a first portion of the transaction. The first portion of the transaction 108 can include the first n characters in the transaction 108 that include the tokens of the minimized token marker sequence. In this way, the common hash can group similar transactions 108 with different token marker sequences 110. In some embodiments of the present disclosure, the lexer 112 can store the common hash in association with the token marker sequence 110.

Figure 3:
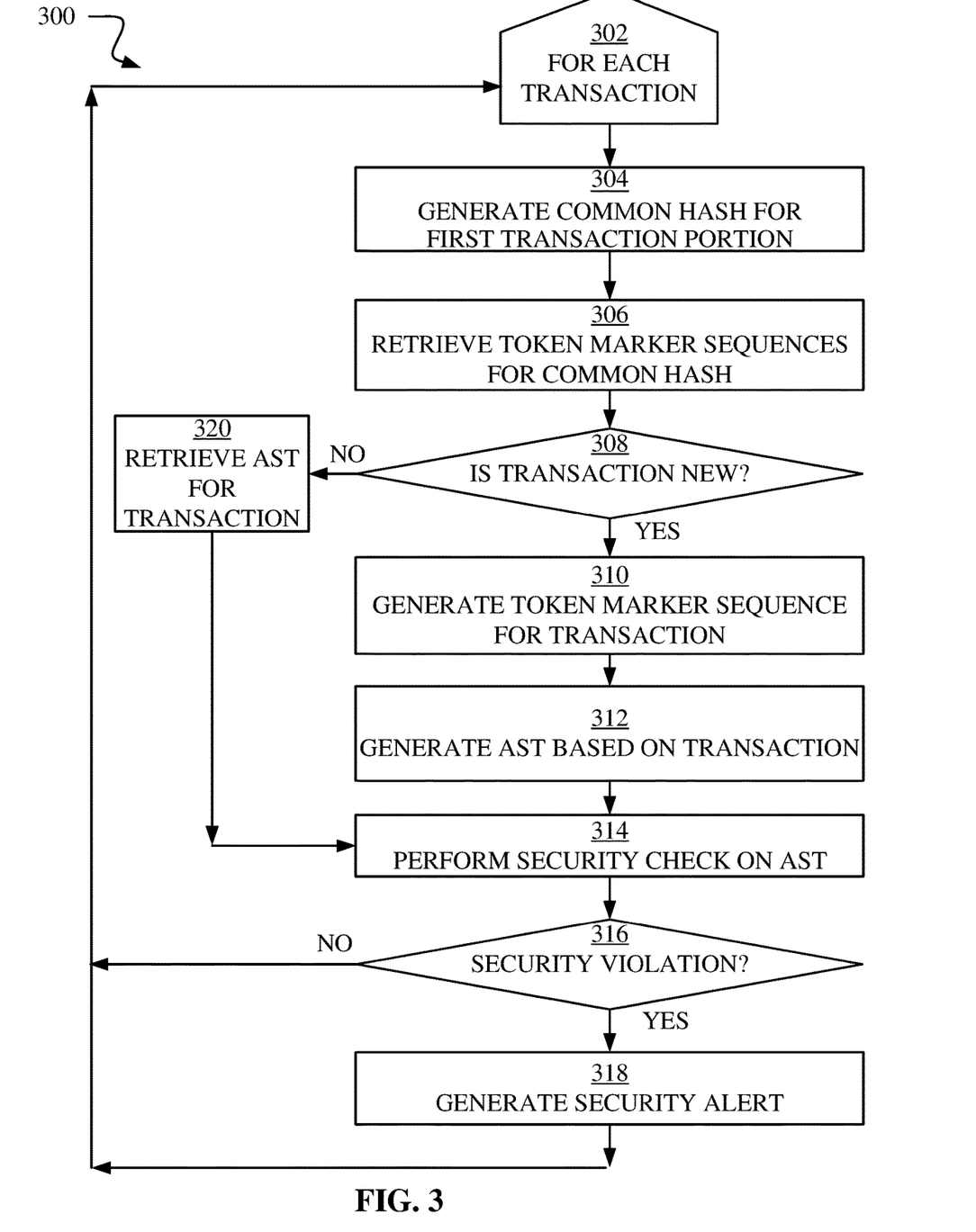
FIG. 3 is a process flow diagram of a method for performing a security check, in accordance with some embodiments of the present disclosure.

FIG. 3 is a process flow diagram of a method 300 for performing a security check, in accordance with some embodiments of the present disclosure. The method 300 can be performed by a DPS, such as the DPS 104 described with respect to FIG. 1. The DPS 104 can perform the operations 302 through 320 for each transaction 108 of a transaction stream.

At operation 304, the DPS 104 can generate a common hash for a first portion of the transaction 108. As stated previously, the DPS 104 can use the common hash to similar group transactions. The common hash can be generated based on a predetermined number of the first characters in the transaction.

At operation 306, the DPS 104 can retrieve token marker sequences 110 for the common hash. The token marker sequences 110 can be the token marker sequences 110 described with respect to FIG. 1.

At operation 308, the DPS 104 can determine if the transaction is new based on the retrieved token marker sequences 110. If there are no token marker sequences 110 for the common hash, the DPS 104 can determine that the transaction is new and flow to operation 310. Additionally, if the retrieved token sequences do not match the generated token marker sequence 110 for the transaction, the method 300 can flow to operation 320.

At operation 310, the DPS 104 can generate the token marker sequence 110 for the transaction 108. More specifically, the lexer 112 can generate the token marker sequence 110, as described with respect to FIG. 2.

At operation 312, the DPS 104 can generate an AST 116 for the transaction 108. More specifically, the parser 114 can generate the AST 116 for the transaction 108.

At operation 314, the DPS 104 can perform a security check on the generated AST 116. The security check can involve identifying potential security violations or anomalies.

At operation 316, the DPS 104 can determine if there is a security violation. If there is a security violation, the method 300 can flow to operation 318. If there is no security violation, the method 300 can flow to operation 302 for the next transaction.

At operation 318, the DPS 104 can generate a security alert. Generating the security alert can involve generating a message for review by a system administrator, for example. The security alert can identify the transaction where the security violation is identified and the potential security violation.

If at operation 308, the DPS 104 determines that the transaction 108 is not new, control may flow to operation 320. If the transaction 108 is not new, the parser 114 has already generated the AST 116 for the transaction 108. Accordingly, at operation 320, the DPS 104 can retrieve the AST 116 for the transaction 108. Further, control may flow to operation 316, where the DPS 104 can check the retrieved AST 116 for a security violation. In this way, the DPS 104 can avoid the cost of generating duplicate ASTS for duplicated (or relatively similar) transactions.

Figure 4A:
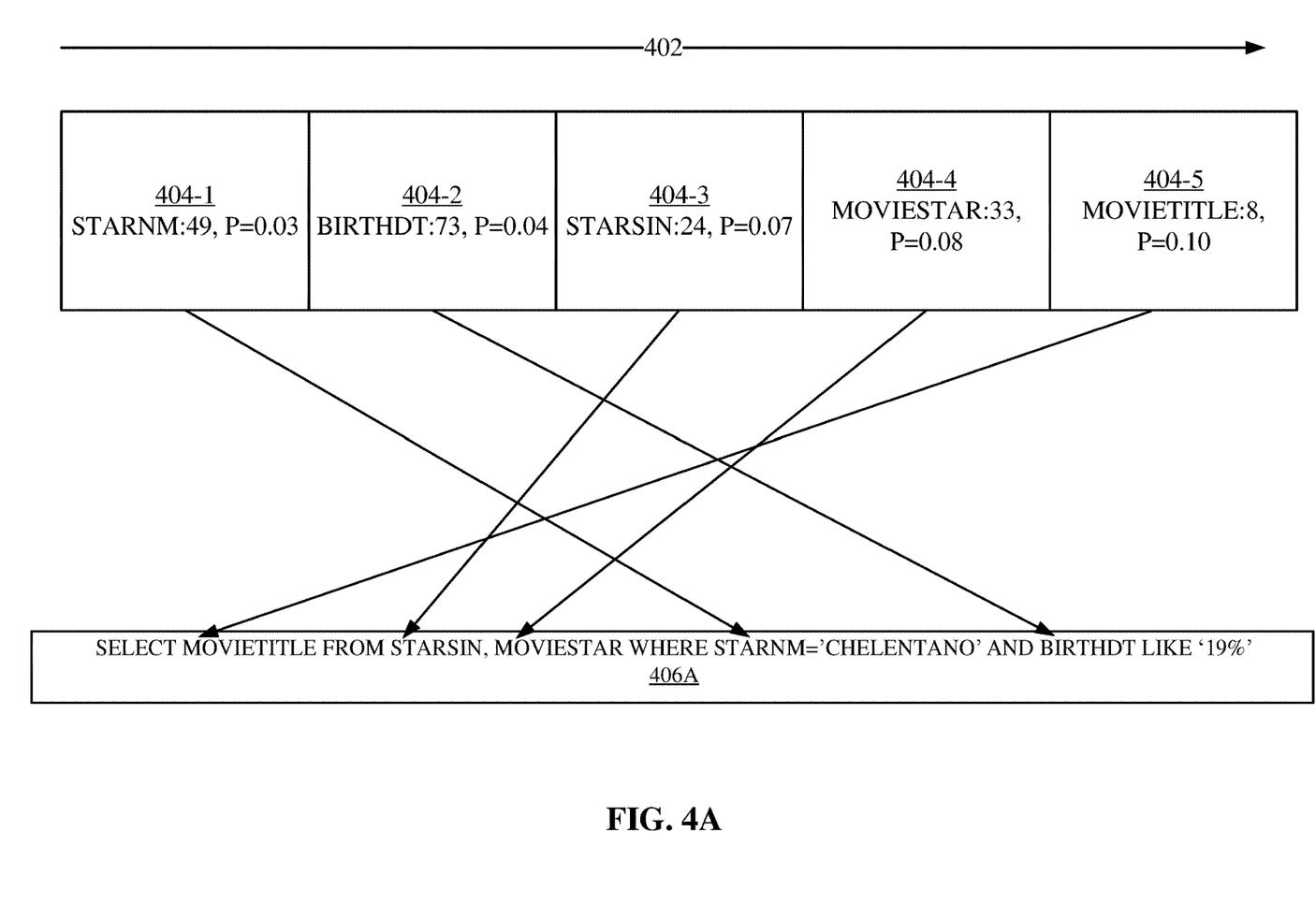
FIG. 4A is a block diagram of a comparison of a token marker sequence to a transaction, in accordance with some embodiments of the present disclosure.

FIG. 4A is a block diagram of a comparison of token marker sequences 110 to a transaction 406A, in accordance with some embodiments of the present disclosure. The line 402 represents the direction in which the DPS 104 can compare the token markers 404 of a retrieved token marker sequence 110 to the tokens of a transaction 406A. The token markers 404 include the token name (abbreviated for clarity), the position of the token, and the probability of appearing in the transaction stream. In some embodiments, the tokens can be ordered in ascending order based on probability. In this example, the lines from the token markers 404 to the tokens of the transaction 406A represent matches between the retrieved token marker sequence 110 and the transaction 406A. Thus, the line from token marker 404-1 points to the token, STARNM, at position 49 in the transaction 406A. Further, the line from token marker 404-2 points to the token, BIRTHDT, at position 73 in the transaction 406A. Additionally, the line from token marker 404-3 points to the token, STARSIN, at position 24 in the transaction 406A. Also, the line from token marker 404-4 points to the token, MOVIESTAR, at position 33 in the transaction 406A. Further, the line from token marker 404-5 points to the token, MOVIETITLE, at position 8 in the transaction 406A. In this example, the retrieved token marker sequence 110 matches the transaction 406A. Thus, the DPS 104 can retrieve a previously generated AST 116 for the transaction 406A to perform the security check.

Figure 4B:
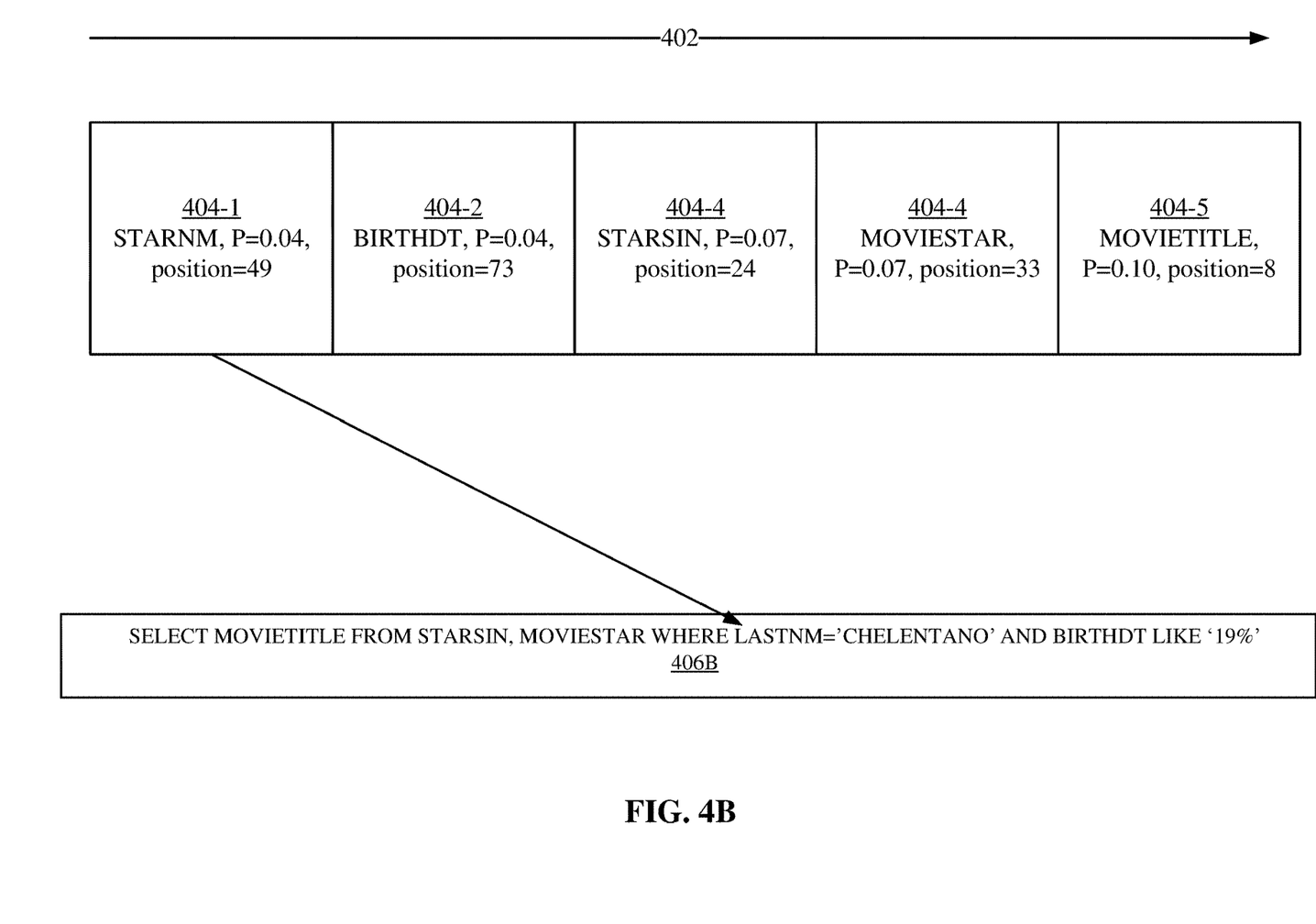
FIG. 4B is a block diagram of a comparison of a token marker sequence to a transaction, in accordance with some embodiments of the present disclosure.

FIG. 4B is a block diagram of a comparison of a token marker sequences 110 to a transaction 406B, in accordance with some embodiments of the present disclosure. The line 402 represents the direction in which the DPS 104 can compare the token markers 404 of a retrieved token marker sequence 110 to the tokens of a transaction 406B. In this example, the line from the token marker 404-1 to position 49 of the transaction 406B indicates a mismatch between the token marker sequence 110 and the transaction 406B. Accordingly, the parser 114 can generate a new AST for the transaction 406B. Advantageously, the DPS 104 can relatively quickly detect a difference between the token marker sequence 110 of a previously processed transaction and a current transaction.

The complexity of such an approach in the worst case can be linear, $\sim O(n)$, where n is the size of the transaction. Further, in some embodiments of the present disclosure, the DPS 104 can perform the comparisons of existing token marker sequences 110 to transactions in parallel processes. Using parallel processes, the DPS 104 can reduce the complexity to $\sim O(n/m)$, where m represents the number of parallel threads. These approaches provide an advantage over existing techniques where the worst-case complexity can be approximately $O(n^4)$.

Figure 5:
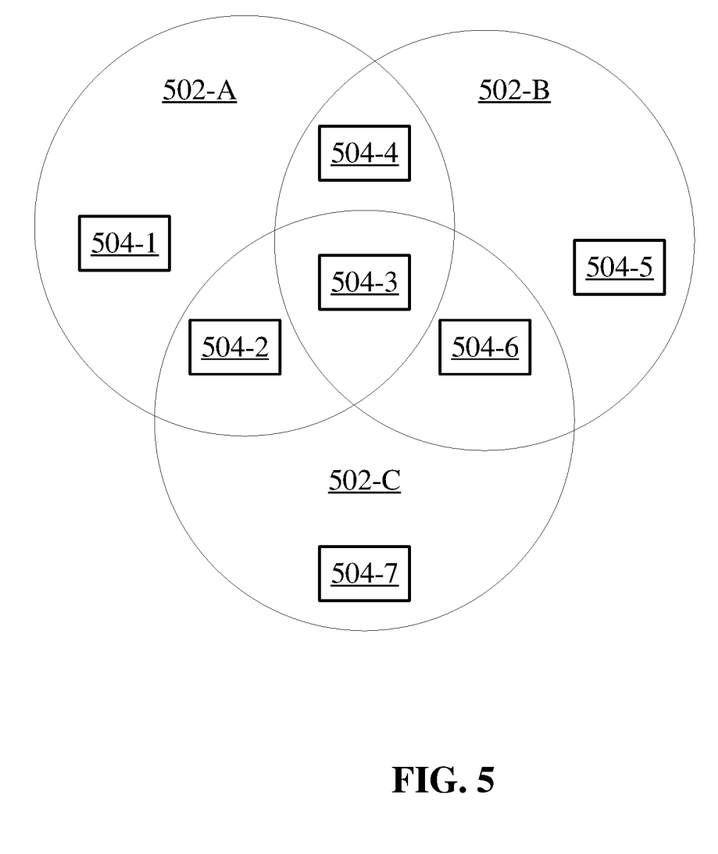
FIG. 5 is a Venn diagram of example transactions with shared tokens, in accordance with some embodiments of the present disclosure.

FIG. 5 is a Venn diagram 500 of example transactions with shared tokens, in accordance with some embodiments of the present disclosure. The Venn diagram 500 includes symbolic representations of transactions 502-A, 502-B, and 502-C containing tokens 504-1 through 504-7. In this example, transaction 502-A includes tokens 504-1 through 504-4. Further, transaction 502-B includes tokens 504-3 through 504-6. Additionally, transaction 502-C includes tokens 504-2, 504-3, 504-6, and 504-7. As shown, the transactions 502-A and 502-B share tokens 504-3 and 504-4. Further, the transactions 502-A and 502-C share tokens 504-2 and 504-3. Additionally, the transactions 502-B and 502-C share tokens 504-3 and 504-6.

In this example, the DPS 104 can uniquely identify the transactions 502-A, 502-B, and 502-C by their unique tokens, respectively, tokens 504-1, 504-5, and 504-7. Thus, the DPS 104 can maintain token marker sequences 110 as minimal size sets that uniquely identify the transactions 108.

As described herein, some embodiments of the present disclosure can generate representations of relatively large transactions using token marker sequences 110 sorted in ascending order of the probability that each token appears in a stream of transactions. The token marker sequences 110 can include the token names and the positions of the tokens within a transaction. Further, the DPS 104 can minimize the size of the token marker sequences 110 to only that which is useful for uniquely identifying transactions. By minimizing the size of the token marker sequences 110, the DPS 104 can save time in comparing token marker sequences 110 to new transactions. Further, comparing token marker sequences 110 to new transactions makes it possible for the DPS 104 to determine whether the parser 114 has already generated an AST 116 for the transaction, thus avoiding the relatively slow, time-consuming process of re-generating a duplicate AST 116.

Figure 6:
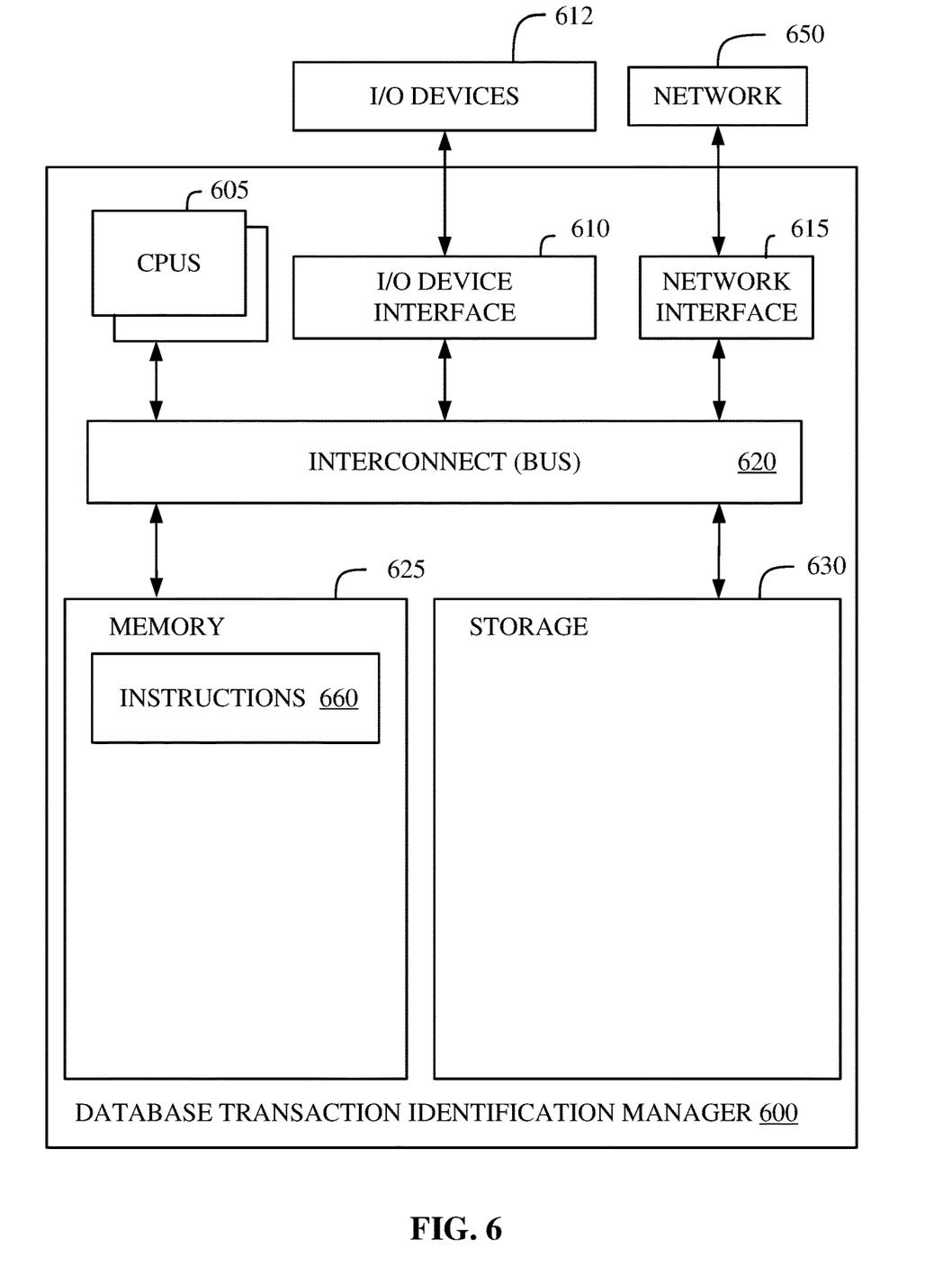
FIG. 6 is a block diagram of an example database transaction identification manager, in accordance with some embodiments of the present disclosure.

FIG. 6 is a block diagram of an example database transaction identification manager 600, in accordance with some embodiments of the present disclosure. In various embodiments, the database transaction identification manager 600 is similar to the lexer 112 and can perform the methods described in FIGS. 2 and 3, and/or the functionality discussed in FIGS. 1, 4A, 4B, and 5. In some embodiments, the database transaction identification manager 600 provides instructions for the aforementioned methods and/or functionalities to a client machine such that the client machine executes the method, or a portion of the method, based on the instructions provided by the database transaction identification manager 600. In some embodiments, the database transaction identification manager 600 comprises software executing on hardware incorporated into a plurality of devices.

The database transaction identification manager 600 includes a memory 625, storage 630, an interconnect (e.g., BUS) 620, one or more CPUs 605 (also referred to as processors 605 herein), an I/O device interface 610, I/O devices 612, and a network interface 615.

Each CPU 605 retrieves and executes programming instructions stored in the memory 625 or the storage 630. The interconnect 620 is used to move data, such as programming instructions, between the CPUs 605, I/O device interface 610, storage 630, network interface 615, and memory 625. The interconnect 620 can be implemented using one or more busses. The CPUs 605 can be a single CPU, multiple CPUs, or a single CPU having multiple processing cores in various embodiments. In some embodiments, a CPU 605 can be a digital signal processor (DSP). In some embodiments, CPU 605 includes one or more 3D integrated circuits (3DICs) (e.g., 3D wafer-level packaging (3DWLP), 3D interposer based integration, 3D stacked ICs (3D-SICs), monolithic 3D ICs, 3D heterogeneous integration, 3D system in package (3DSiP), and/or package on package (PoP) CPU configurations). Memory 625 is generally included to be representative of random access memory (e.g., static random access memory (SRAM), dynamic random access memory (DRAM), or Flash). The storage 630 is generally included to be representative of non-volatile memory, such as a hard disk drive, solid-state device (SSD), removable memory cards, optical storage, and/or flash memory devices. Additionally, the storage 630 can include storage area network (SAN) devices, the cloud, or other devices connected to the database transaction identification manager 600 via the I/O device interface 610 or to a network 650 via the network interface 615.

In some embodiments, the memory 625 stores instructions 660. However, in various embodiments, the instructions 660 are stored partially in memory 625 and partially in storage 630, or they are stored entirely in memory 625 or entirely in storage 630, or they are accessed over a network 650 via the network interface 615.

Instructions 660 can be processor-executable instructions for performing any portion of, or all, any of the methods described in FIGS. 2 and 3, and/or the functionality discussed in FIGS. 1, 4A, 4B, and 5.

In various embodiments, the I/O devices 612 include an interface capable of presenting information and receiving input. For example, I/O devices 612 can present information to a listener interacting with database transaction identification manager 600 and receive input from the listener.

The database transaction identification manager 600 is connected to the network 650 via the network interface 615. Network 650 can comprise a physical, wireless, cellular, or different network.

In some embodiments, the database transaction identification manager 600 can be a multi-user mainframe computer system, a single-user system, or a server computer or similar device that has little or no direct user interface but receives requests from other computer systems (clients). Further, in some embodiments, the database transaction identification manager 600 can be implemented as a desktop computer, portable computer, laptop or notebook computer, tablet computer, pocket computer, telephone, smartphone, network switches or routers, or any other appropriate type of electronic device.

It is noted that FIG. 6 is intended to depict the major representative components of an exemplary database transaction identification manager 600. In some embodiments, however, individual components can have greater or lesser complexity than as represented in FIG. 6, components other than or in addition to those shown in FIG. 6 can be present, and the number, type, and configuration of such components can vary.

Although this disclosure includes a detailed description on cloud computing, implementation of the teachings recited herein are not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model can include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but can be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It can be managed by the organization or a third-party and can exist on-premises or off-premises.

Community cloud: the cloud infrastructure is shared by several organizations and supports a specific community that has shared concerns (e.g., mission, security requirements, policy, and compliance considerations). It can be managed by the organizations or a third-party and can exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service-oriented with a focus on statelessness, low coupling, modularity, and semantic interoperability. At the heart of cloud computing is an infrastructure that includes a network of interconnected nodes.

Figure 7:
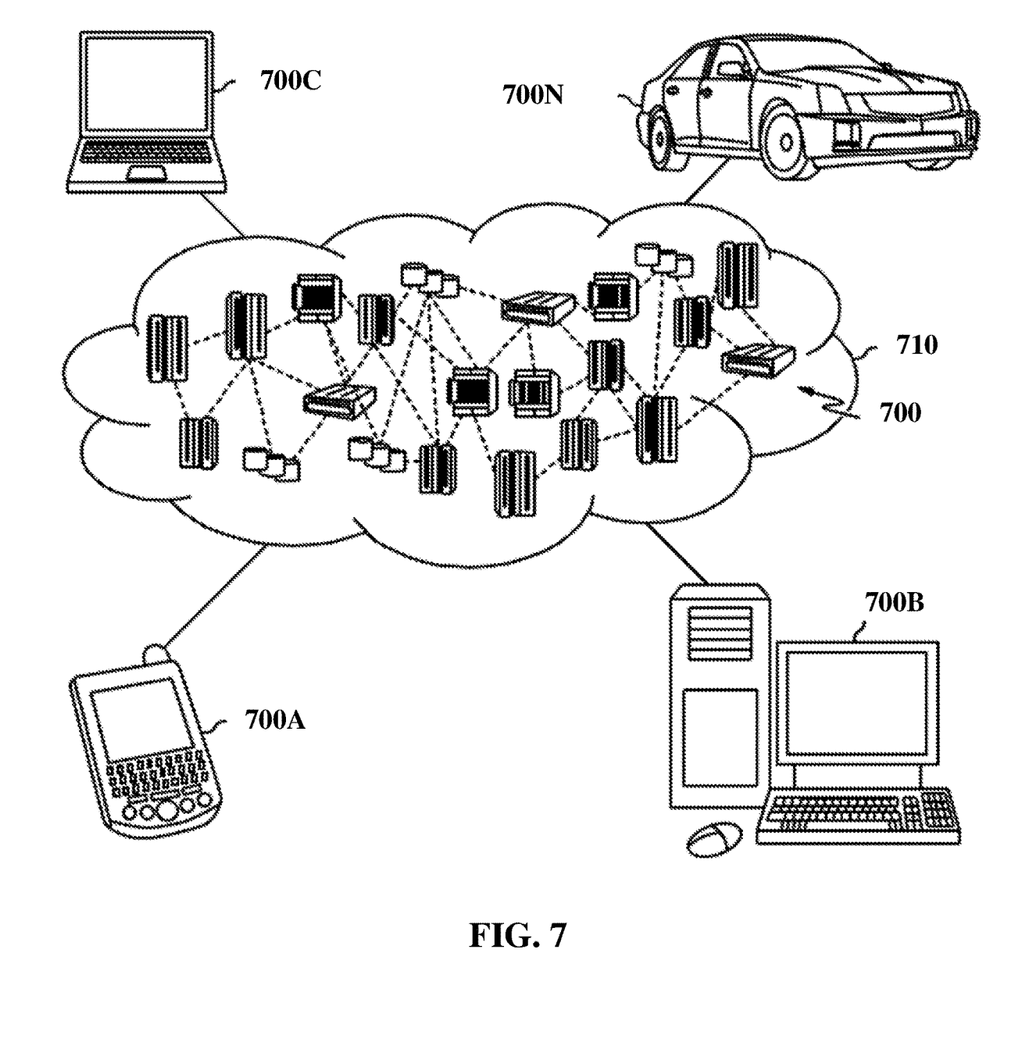
FIG. 7 is a cloud computing environment, according to some embodiments of the present disclosure.

FIG. 7 is a cloud computing environment 710, according to some embodiments of the present disclosure. As shown, cloud computing environment 710 includes one or more cloud computing nodes 700. The cloud computing nodes 700 can perform the methods described in FIGS. 2 and 3, and/or the functionality discussed in FIGS. 1, 4A, 4B, and 5. Additionally, cloud computing nodes 700 can communicate with local computing devices used by cloud consumers, such as, for example, personal digital assistant (PDA) or cellular telephone 700A, desktop computer 700B, laptop computer 700C, and/or automobile computer system 700N. Further, the cloud computing nodes 700 can communicate with one another. The cloud computing nodes 700 can also be grouped (not shown) physically or virtually, in one or more networks, such as Private, Community, Public, or Hybrid clouds as described hereinabove, or a combination thereof. This allows cloud computing environment 710 to offer infrastructure, platforms and/or software as services for which a cloud consumer does not need to maintain resources on a local computing device. It is understood that the types of computing devices 700A-N shown in FIG. 7 are intended to be illustrative only and that computing nodes 700 and cloud computing environment 710 can communicate with any type of computerized device over any type of network and/or network addressable connection (e.g., using a web browser).

Figure 8:
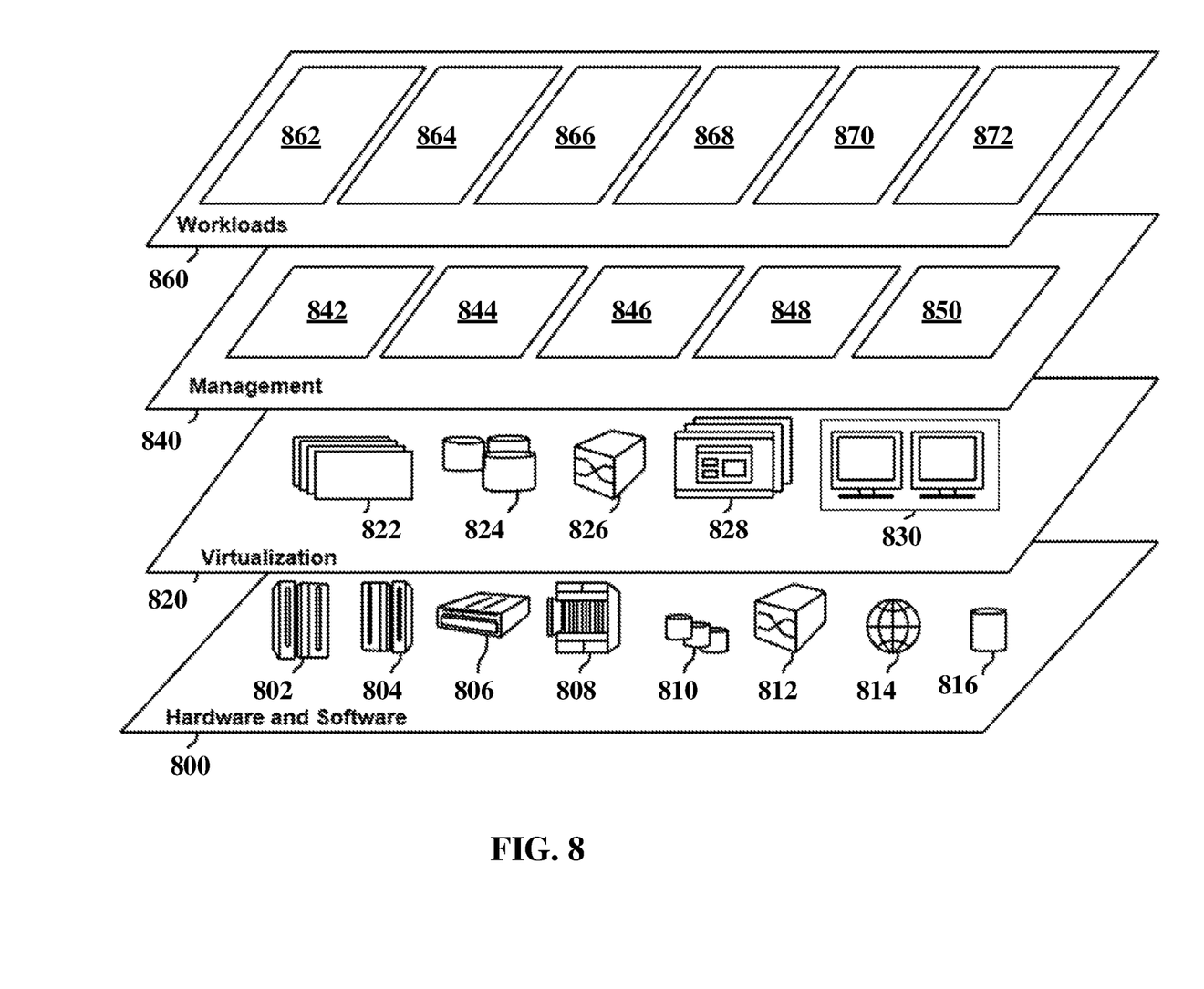
FIG. 8 is a set of functional abstraction model layers provided by cloud computing environment, according to some embodiments of the present disclosure, is shown.

FIG. 8 is a set of functional abstraction model layers provided by cloud computing environment 710 (FIG. 7), according to some embodiments of the present disclosure. It should be understood in advance that the components, layers, and functions shown in FIG. 8 are intended to be illustrative only and embodiments of the disclosure are not limited thereto. As depicted below, the following layers and corresponding functions are provided.

Hardware and software layer 800 includes hardware and software components. Examples of hardware components include: mainframes 802; RISC (Reduced Instruction Set Computer) architecture based servers 804; servers 806; blade servers 808; storage devices 810; and networks and networking components 812. In some embodiments, software components include network application server software 814 and database software 816.

Virtualization layer 820 provides an abstraction layer from which the following examples of virtual entities can be provided: virtual servers 822; virtual storage 824; virtual networks 826, including virtual private networks; virtual applications and operating systems 828; and virtual clients 830.

In one example, management layer 840 can provide the functions described below. Resource provisioning 842 provides dynamic procurement of computing resources and other resources that are utilized to perform tasks within the cloud computing environment. Metering and Pricing 844 provide cost tracking as resources are utilized within the cloud computing environment, and billing or invoicing for consumption of these resources. In one example, these resources can include application software licenses. Security provides identity verification for cloud consumers and tasks, as well as protection for data and other resources. User portal 846 provides access to the cloud computing environment for consumers and system administrators. Service level management 848 provides cloud computing resource allocation and management such that required service levels are met. Service level management 848 can allocate suitable processing power and memory to process static sensor data. Service Level Agreement (SLA) planning and fulfillment 850 provide pre-arrangement for, and procurement of, cloud computing resources for which a future requirement is anticipated in accordance with an SLA.

Workloads layer 860 provides examples of functionality for which the cloud computing environment can be utilized. Examples of workloads and functions which can be provided from this layer include: mapping and navigation 862; software development and lifecycle management 864; virtual classroom education delivery 866; data analytics processing 868; transaction processing 870; and database transaction identification manager 872.

The present disclosure may be a system, a method, and/or a computer program product at any possible technical detail level of integration. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method for identifying database transactions, comprising:
    generating a unique identifier for a database transaction by:
        generating a token marker sequence of the database transaction, wherein the token marker sequence comprises a plurality of token markers, and wherein one of the plurality of token markers comprises:
            a token of the database transaction; and
            a position corresponding to the token of the database transaction;
        sorting the plurality of token markers based on a probability of each token occurring in a stream of database transactions comprising the database transaction; and
        reducing a size of the token marker sequence based on a first predetermined threshold, wherein the unique identifier for the database transaction comprises the token marker sequence having the reduced size;
    generating a hash of a portion of the database transaction;
    retrieving a plurality of token marker sequences associated with the hash;
    determining whether the database transaction is a duplicate of a previous database transaction based on the retrieved token marker sequences;
    performing, in response to a determination that the database transaction is the duplicate of the previous database transaction, a security validation on an abstract syntax tree (AST) for the previous database transaction; and
    determining whether the database transaction represents a security threat based on the security validation.

2. The computer-implemented method of claim 1, wherein the plurality of token marker sequences comprise a subset of tokens of the database transaction, wherein the subset of tokens comprises a plurality of encountered tokens of the database transaction in the stream of database transactions, wherein a frequency of the plurality of encountered tokens is less than a second predetermined threshold.

3. The computer-implemented method of claim 2, wherein the portion of the database transaction comprises a predetermined number of characters starting at a first character of the database transaction.

4. The computer-implemented method of claim 2, further comprising:
    determining that the database transaction is not the duplicate of the previous database transaction;
    generating a new token marker sequence based on the database transaction; and
    storing the new token marker sequence in association with the hash.

5. The computer-implemented method of claim 4, wherein generating the new token marker sequence comprises:
    generating an additional plurality of token markers for a corresponding plurality of tokens of the database transaction;
    sorting the additional plurality of token markers based on a probability of the corresponding plurality of tokens appearing in the stream of database transactions comprising the database transaction; and reducing a size of the new token marker sequence based on a difference between the database transaction and one or more other database transactions of the stream of transactions.

6. The computer-implemented method of claim 5, wherein the additional plurality of token markers comprise the tokens and a character position within the database transaction where a first character of the token is disposed.

7. The computer-implemented method of claim 5, further comprising:
    generating a new AST for the database transaction; and
    associating the new AST with the token marker sequence.

8. A computer program product comprising program instructions stored on a computer readable storage medium, the program instructions executable by a processor to cause the processor to perform a method comprising:
    generating a unique identifier for a database transaction by:
        generating a token marker sequence of the database transaction, wherein the token marker sequence comprises a plurality of token markers, and wherein one of the plurality of token markers comprises:
            a token of the database transaction; and
            a position corresponding to the token of the database transaction;
        sorting the plurality of token markers based on a probability of each token occurring in a stream of database transactions comprising the database transaction; and
        reducing a size of the token marker sequence based on a first predetermined threshold, wherein the unique identifier for the database transaction comprises the token marker sequence having the reduced size;
    generating a hash of a portion of the database transaction;
    retrieving a plurality of token marker sequences associated with the hash;
    determining whether the database transaction is a duplicate of a previous database transaction based on the retrieved token marker sequences;
    performing, in response to a determination that the database transaction is the duplicate of the previous database transaction, a security validation on an abstract syntax tree (AST) for the previous database transaction; and
    determining whether the database transaction represents a security threat based on the security validation.

9. The computer program product of claim 8, wherein the plurality of token marker sequences comprise a subset of tokens of the database transaction, wherein the subset of tokens comprises a plurality of encountered tokens of the database transaction in the stream of database transactions, wherein a frequency of the plurality of encountered tokens is less than a second predetermined threshold.

10. The computer program product of claim 9, wherein the portion of the database transaction comprises a predetermined number of characters starting at a first character of the database transaction.

11. The computer program product of claim 9, further comprising:
    determining that the database transaction is not the duplicate of the previous database transaction;
    generating a new token marker sequence based on the database transaction; and
    storing the new token marker sequence in association with the hash.

12. The computer program product of claim 11, wherein generating the new token marker sequence comprises:
    generating an additional plurality of token markers for a corresponding plurality of tokens of the database transaction;
    sorting the additional plurality of token markers based on a probability of the corresponding plurality of tokens appearing in the stream of database transactions comprising the database transaction; and
    reducing a size of the new token marker sequence based on a difference between the database transaction and one or more other database transactions of the stream of transactions.

13. The computer program product of claim 12, wherein the additional plurality of token markers comprise the tokens and a character position within the database transaction where a first character of the token is disposed.

14. The computer program product of claim 12, further comprising:
    generating a new AST for the database transaction; and
    associating the new AST with the token marker sequence.

15. A system comprising:
    a computer processing circuit; and
    a computer-readable storage medium storing instructions, which, when executed by the computer processing circuit, are configured to cause the computer processing circuit to perform a method comprising:
    generating a unique identifier for a database transaction by:
        generating a token marker sequence of the database transaction, wherein the token marker sequence comprises a plurality of token markers, and wherein one of the plurality of token markers comprises:
            a token of the database transaction; and
            a position corresponding to the token of the database transaction;
        sorting the plurality of token markers based on a probability of each token occurring in a stream of database transactions comprising the database transaction;
        reducing a size of the token marker sequence based on a first predetermined threshold, wherein the unique identifier for the database transaction comprises the token marker sequence having the reduced size;
    generating a hash of a portion of the database transaction;
    retrieving a plurality of token marker sequences associated with the hash;
    determining whether the database transaction is a duplicate of a previous database transaction based on the retrieved token marker sequences;
    performing, in response to a determination that the database transaction is the duplicate of the previous database transaction, a security validation on an abstract syntax tree (AST) for the previous database transaction; and
    determining whether the database transaction represents a security threat based on the security validation.

16. The system of claim 15, wherein the plurality of token marker sequences comprise a subset of tokens of the database transaction, wherein the subset of tokens comprises a plurality of encountered tokens of the database transaction in the stream of database transactions, wherein a frequency of the plurality of encountered tokens is less than a second predetermined threshold.

17. The system of claim 16, wherein the portion of the database transaction comprises a predetermined number of characters starting at a first character of the database transaction.

\* \* \* \* \*